(12) United States Patent
Schumacher

(10) Patent No.: US 8,088,152 B2
(45) Date of Patent: Jan. 3, 2012

(54) ORTHOPEDIC RETAINING SYSTEM

(75) Inventor: Joerg Schumacher, Teltow (DE)

(73) Assignee: Aesculap AG, Tuttlingen (DE)

( * ) Notice: Subject to any disclaimer, the term of this patent is extended or adjusted under 35 U.S.C. 154(b) by 601 days.

(21) Appl. No.: 12/231,322

(22) Filed: Aug. 28, 2008

(65) Prior Publication Data

US 2009/0062865 A1    Mar. 5, 2009

(30) Foreign Application Priority Data

Aug. 30, 2007  (DE) .................. 10 2007 042 953

(51) Int. Cl.
*A61B 17/04* (2006.01)

(52) U.S. Cl. ........ 606/328; 606/265; 606/272; 606/300; 606/266; 606/264

(58) Field of Classification Search .................. 606/300, 606/301, 305, 306, 308, 309, 313, 319, 324, 606/328; 411/15

See application file for complete search history.

(56) References Cited

U.S. PATENT DOCUMENTS

| | | | |
|---|---|---|---|
| 2,384,953 A | | 9/1945 | Miller |
| 5,207,678 A | | 5/1993 | Harms et al. |
| 5,474,555 A | | 12/1995 | Puno et al. |
| 5,716,356 A | * | 2/1998 | Biedermann et al. ......... 606/271 |
| 5,810,819 A | | 9/1998 | Errico et al. |
| 6,077,262 A | * | 6/2000 | Schlapfer et al. ............. 606/305 |
| 6,090,111 A | | 7/2000 | Nichols |
| 6,251,112 B1 | | 6/2001 | Jackson |
| 6,485,492 B1 | | 11/2002 | Halm et al. |
| 6,565,565 B1 | | 5/2003 | Yuan et al. |
| 7,211,086 B2 | | 5/2007 | Biedermann et al. |
| 7,223,268 B2 | | 5/2007 | Biedermann |
| 2003/0100904 A1 | * | 5/2003 | Biedermann .................... 606/73 |
| 2003/0125741 A1 | * | 7/2003 | Biedermann et al. ........... 606/61 |
| 2003/0153911 A1 | * | 8/2003 | Shluzas ........................... 606/61 |
| 2003/0199873 A1 | | 10/2003 | Richelsoph |
| 2004/0097933 A1 | | 5/2004 | Lourdel et al. |
| 2004/0236330 A1 | * | 11/2004 | Purcell et al. ................... 606/61 |
| 2005/0119667 A1 | | 6/2005 | Leport et al. |
| 2005/0131410 A1 | | 6/2005 | Lin |
| 2005/0203516 A1 | | 9/2005 | Biedermann et al. |
| 2005/0267472 A1 | * | 12/2005 | Biedermann et al. ........... 606/61 |
| 2006/0009773 A1 | | 1/2006 | Jackson |

(Continued)

FOREIGN PATENT DOCUMENTS

| | | |
|---|---|---|
| DE | 41 10 002 | 5/1992 |
| DE | 41 07 480 | 9/1992 |
| DE | 198 35 816 | 2/2000 |

(Continued)

*Primary Examiner* — Thomas C. Barrett
*Assistant Examiner* — Melissa A Golob
(74) *Attorney, Agent, or Firm* — Lipsitz & McAllister, LLC

(57) ABSTRACT

An orthopedic retaining system comprising at least one bone screw which has a head part and a threaded shaft pivotally mounted thereon is disclosed. A clamping element is mounted in the head part, which can be pressed against the threaded shaft from its upper side and, as a result, secure the threaded shaft relative to the head part. A retaining bar is arranged in a receptacle of the head part and extends essentially transversely to the threaded shaft. A clamping device is provided on the upper side of the head part, by means of which the clamping element and the retaining bar are pressed into the head part such that the threaded shaft and the retaining bar are secured in position relative to the head part. The clamping device comprises an elastically deformable pressure element which is displaced into a clamping position during actuation of the clamping device.

17 Claims, 4 Drawing Sheets

U.S. PATENT DOCUMENTS

| | | |
|---|---|---|
| 2006/0036252 A1 | 2/2006 | Baynham et al. |
| 2006/0095038 A1* | 5/2006 | Jackson .......................... 606/61 |
| 2006/0167455 A1 | 7/2006 | Clement et al. |
| 2006/0293664 A1 | 12/2006 | Schumacher |
| 2007/0260246 A1 | 11/2007 | Biedermann |
| 2007/0286703 A1* | 12/2007 | Doubler et al. ............... 411/433 |
| 2008/0294202 A1 | 11/2008 | Peterson et al. |

FOREIGN PATENT DOCUMENTS

| | | |
|---|---|---|
| DE | 299 23 489 | 11/2000 |
| DE | 101 57 814 | 6/2003 |
| DE | 101 64 323 | 6/2003 |
| DE | 10 2005 021 879 | 11/2006 |
| WO | 2004/047657 | 6/2004 |
| WO | WO2006116606 | * 11/2006 |

* cited by examiner

ORTHOPEDIC RETAINING SYSTEM

This application claims the benefit of German patent application no. 10 2007 042 953.5 filed Aug. 30, 2007, which is incorporated herein and made a part hereof by reference.

BACKGROUND OF THE INVENTION

The invention relates to an orthopedic retaining system comprising at least one bone screw which has a head part and a threaded shaft pivotally mounted on it, a clamping element which is mounted in the head part, can be pressed against the threaded shaft from the upper side of the head part and, as a result, secures the threaded shaft relative to the head part, a retaining bar which is arranged in a receptacle of the head part and extends essentially transversely to the threaded shaft and a clamping device on the upper side of the head part, by means of which the clamping element and the retaining bar are pressed into the head part in such a manner that the threaded shaft and the retaining bar are secured in position relative to the head part.

Orthopedic retaining systems of this type are used to fix bones and bone fragments in position relative to one another; for this purpose, bone screws are screwed into the bones and bone fragments and then connected to one another by means of the retaining bar such that the orthopedic retaining system comprising the bone screws and the retaining bar forms as such a rigid member which fixes the bones and bone fragments relative to one another in their position. In this respect, it is known to design the head part and the threaded shaft of the clamping screw so as to be pivotable relative to one another, either pivotable in all directions as a result of a ball connection or pivotable about an axis extending transversely to the longitudinal axis of the threaded shaft as a result of a limited mounting. When the orthopedic retaining system is used, it is, therefore, possible to pivot the head part in relation to the threaded shaft and, in addition, displace the retaining bar in relation to the head part; these degrees of freedom are restricted only when the clamping device is actuated, i.e., the pivotability is eliminated when the clamping device is actuated and the free displaceability of the retaining bar. In the case of known devices (DE 10 2005 021 879 A1), this is brought about, for example, by screwing a clamping screw into the head part, this screw being supported on the retaining bar which then rests, for its part, on the clamping element. In this way, the displaceability of the retaining bar and the pivotability of the threaded shaft in relation to the head part are, in any case, terminated at the same time when the clamping device is actuated.

This can be disadvantageous since, for the purpose of aligning the orthopedic retaining system in these arrangements, either the retaining bar is freely displaceable and also the threaded shaft pivotable or, however, both possibilities for movement are blocked.

The object of the invention is to design an orthopedic retaining system in such a manner that the operator has the possibility, with the simplest of means, of curtailing some elements of the movability of head part, retaining bar and threaded shaft whilst still retaining other elements of the movability.

SUMMARY OF THE INVENTION

This object is accomplished in accordance with the invention, in an orthopedic retaining system of the type described at the outset, in that the clamping device comprises an elastically deformable pressure element which, during actuation of the clamping device in the head part in the direction towards its underside, is displaced into a clamping position and abuts first of all on the clamping element and then on the retaining bar with further displacement and elastic deformation.

With such a configuration, the actuation of the clamping device leads first of all to the elastic pressure element abutting on the clamping element and, therefore, to the pivotable threaded shaft being secured in position on the head part while the retaining bar is still freely displaceable. This is not fixed in position until the clamping device is actuated further, the pressure element is also elastically deformed and this elastically deformable pressure element abuts on the retaining bar.

The advantage of this configuration is that the step-wise blocking of the free movability is brought about by one and the same clamping device and so the operator can block the individual movements one after the other with only one tool for actuating the clamping device. By using an elastic pressure element, the operator has, in addition, the possibility of selecting the clamping forces such that when the elastic pressure element abuts on the clamping element the pivotability of the threaded shaft in relation to the head part is restricted but not completely terminated. This enables the operator to pivot the threaded shaft in relation to the head part by using a specific force; the position, once set, is, however, essentially maintained unless the operator readjusts it by applying this force. As a result, the adjustment of the retaining system is simplified since, in this phase, the free pivotability is restricted whereas the free displaceability of the retaining bar is still possible.

The retaining bar can rest on the head part and be supported on it so that, during actuation of the clamping device, the elastic pressure element presses the clamping element against the threaded shaft and, independently thereof, presses the retaining bar against the head part and fixes it in position as a result.

In a preferred embodiment, it is, however, provided for the retaining bar to rest on the clamping element. As a result of this, the elastically deformable pressure element presses the retaining bar against the clamping element when it is displaced into the clamping position and, as a result, presses the clamping element against the threaded shaft, i.e., when the clamping device is actuated completely, the elastic pressure element is not only supported on the clamping element but also exerts additional clamping forces on the clamping element via the retaining bar so that, as a result, a particularly secure fixing in position against all types of movement is possible.

The clamping device can in one preferred embodiment, for example, comprise an actuating element which is displaceable relative to the head part, engages on the elastic pressure element and moves this in the direction towards the clamping position.

The actuating element will preferably be a clamping screw which can be screwed into the head part from the upper side; however, other actuating elements, which engage on the elastic pressure element and displace and deform it, are also possible in this case.

In a first, preferred embodiment, it is provided for the elastic pressure element to be an elastic bracket which bridges the interior space of the head part and the ends of which are supported on the clamping element.

In a further, preferred embodiment, it is provided for the elastic pressure element to be a disc which is arranged in the interior space of the head part, can be elastically deformed and the edge of which is supported on the clamping element. This configuration has the advantage that it is rotationally symmetric and can be used independently of any installation direction of the elastic pressure element.

The actuating element preferably engages the central area of the elastic pressure element and so this is supported on the clamping element first of all with its outer end and is then elastically deformed in the central area by the actuating element when it is actuated further and abuts on the retaining bar.

The elastic pressure element and the actuating element may be designed in one piece.

In another configuration, it is, however, provided for the actuating element and the elastic pressure element to be releasably connected to one another.

The releasable connection can, for example, be an elastic snap-in connection.

It is favorable when the elastic pressure element and the actuating element are rotatable relative to one another about an axis extending concentrically to the longitudinal axis of the head part. In this way, the actuating element, for example, a clamping screw can be turned about this axis without the elastic pressure element being turned; it can rest on the clamping element in a non-rotatable manner.

In a preferred embodiment, it is provided for the clamping element to be a sleeve which is supported on the threaded shaft with its lower edge and on the upper edge of which the elastic pressure element rests.

BRIEF DESCRIPTION OF THE DRAWINGS

The following description of preferred embodiments of the invention serves to explain the invention in greater detail in conjunction with the drawings. These show.

DETAILED DESCRIPTION

Figure 1:
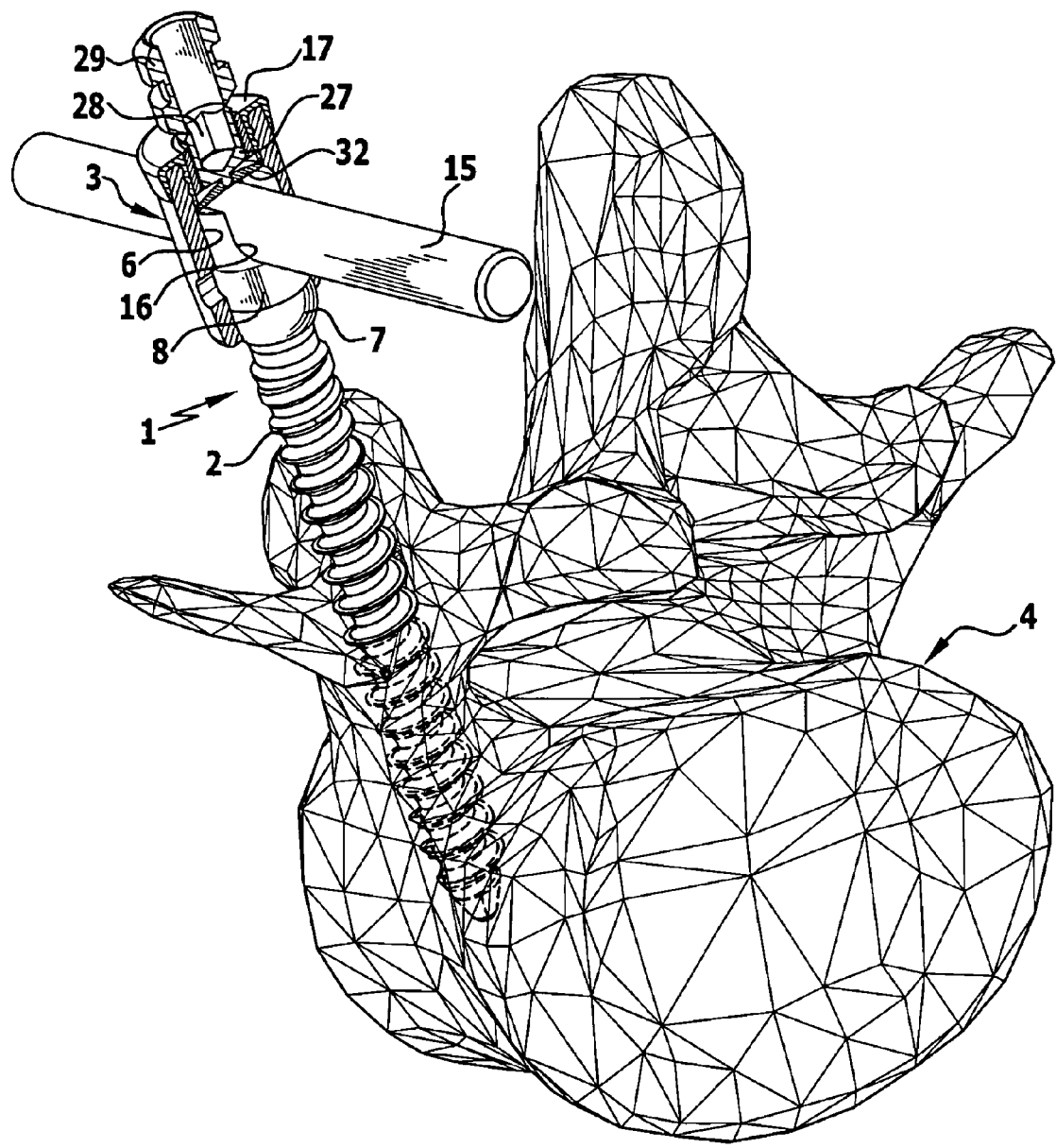
FIG. 1: a vertebral body with an orthopedic retaining system screwed in, this comprising a bone screw and a retaining bar held on it.
Figure 2:
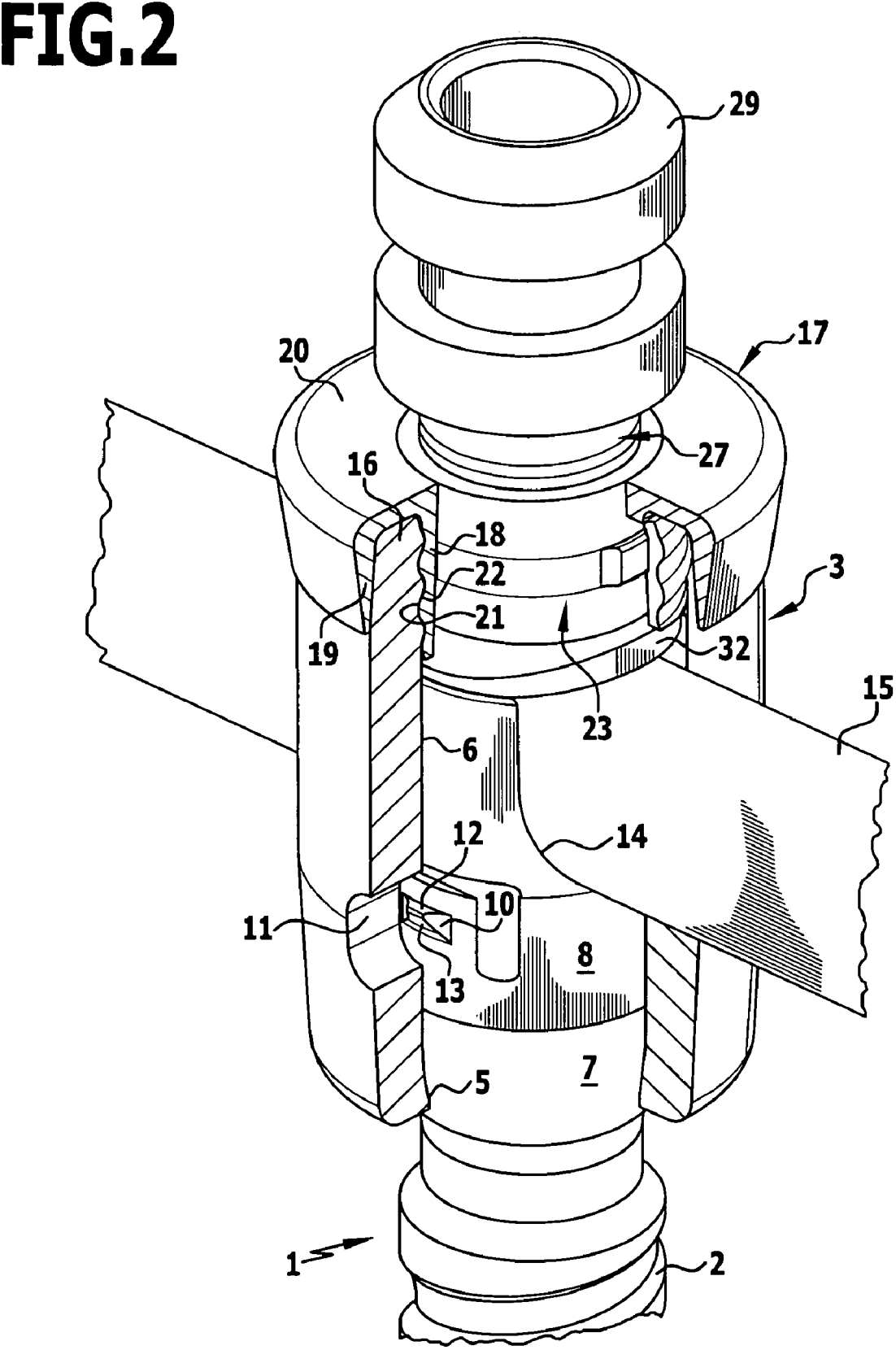
FIG. 2: a perspective view of the head part of the orthopedic retaining system of FIG. 1 with a head part partially cut away.
Figure 3:
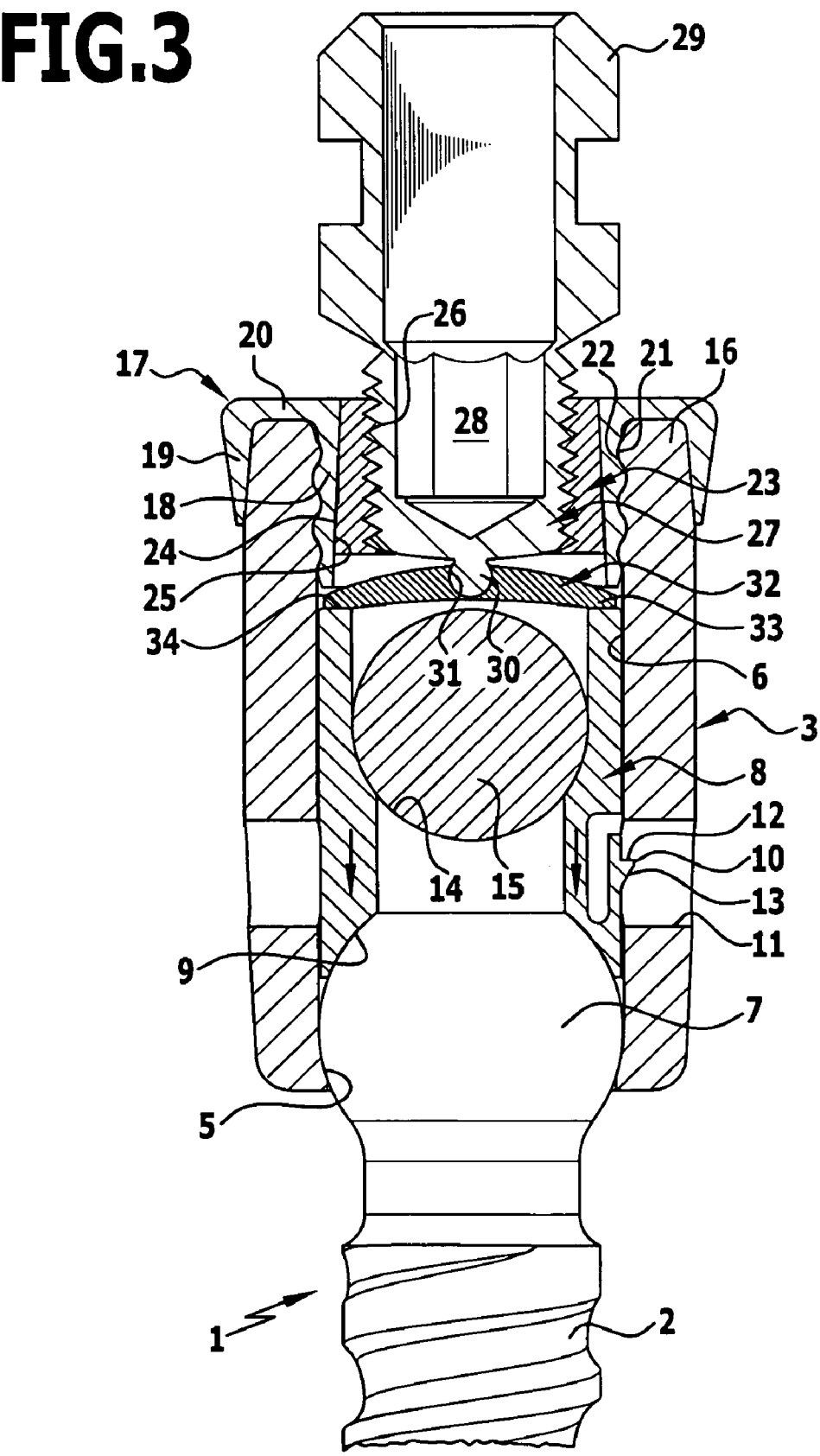
FIG. 3: a cross-sectional view of the head part of FIG. 2 with a threaded shaft secured against any pivoting movement and a retaining bar freely displaceable
Figure 4:
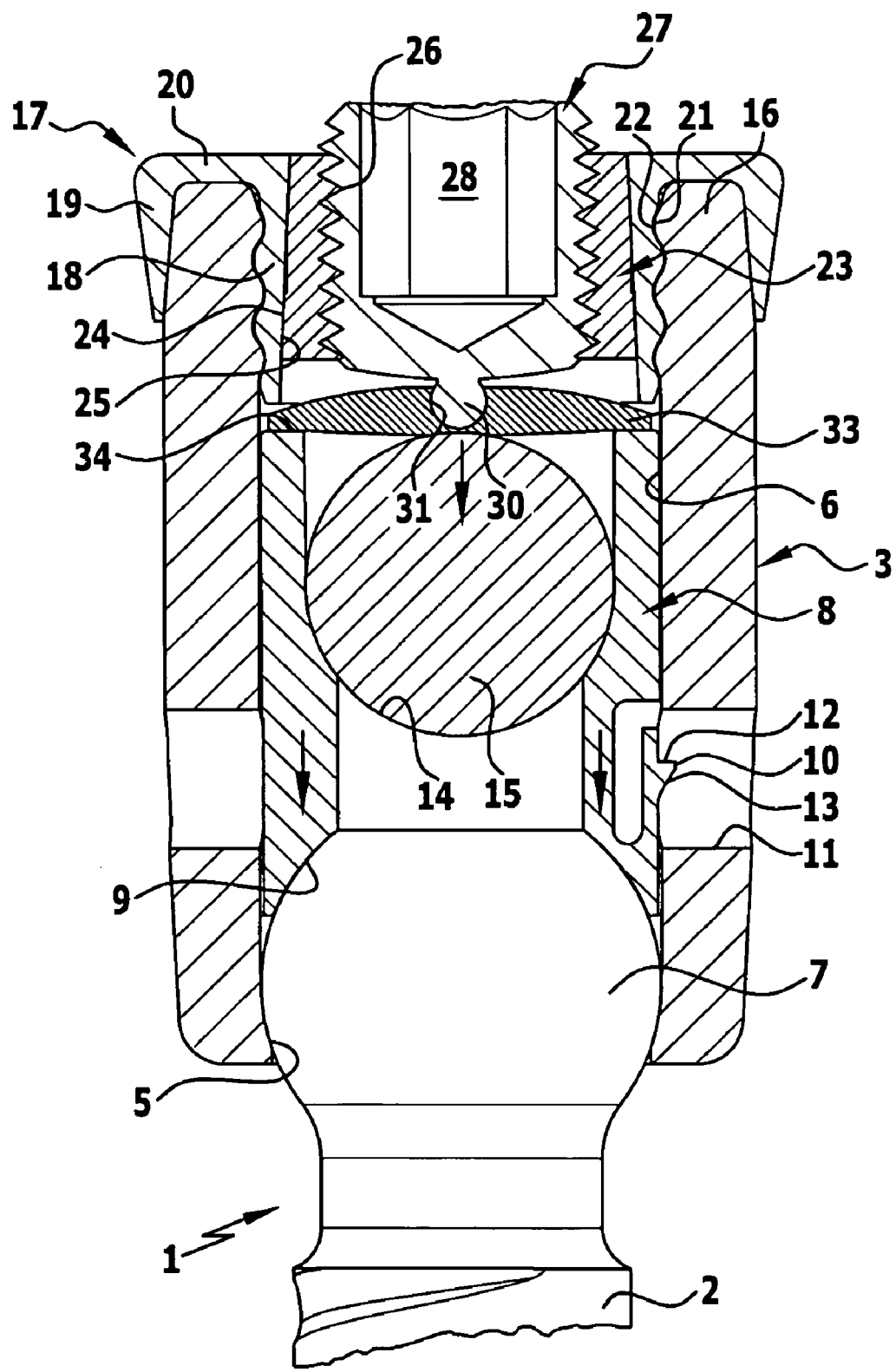
FIG. 4: a view similar to FIG. 3 with a retaining bar secured against any displacement.

The orthopedic retaining system illustrated in the drawings comprises a bone screw 1 with a threaded shaft 2 and a head part 3. The threaded shaft 2 is provided with a bone thread which is preferably self-cutting and can be screwed into a bone, in the embodiment illustrated in FIG. 1 into a vertebral bone 4. The threaded shaft 2 is connected to the head part 3 in the embodiment illustrated so as to be pivotable to all sides. For this purpose, the head part 3, which essentially has the shape of a cylinder sleeve, has a cylindrical interior space 6 which narrows at the lower end in the form of a constriction 5 and into which the threaded shaft 2 can be introduced from above. The threaded shaft 2 has at its upper end a spherical thickened area 7, the outer diameter of which corresponds to the inner diameter of the interior space 6 and which is supported at the lower end on the constriction 5 of the interior space 6 so that a ball-joint connection is formed between the threaded shaft 2 and the head part 3 (FIGS. 3 and 4).

A clamping sleeve 8 is pushed into the interior space 6 from above; the outer diameter of this sleeve corresponds to the inner diameter of the interior space 6 and the sleeve is supported on the upper side of the thickened area 7 with its lower edge 9 which is adapted to the cross section of the thickened area 7. The clamping sleeve 8 supports on one side a radially projecting snap-in nose 10 which can be pressed elastically inwards in a radial direction so that the snap-in nose 10 is positioned within the outer contour of the clamping sleeve 8. In this position of the snap-in nose 10, the clamping sleeve 8 can be pushed into the interior space 6 from above; as soon as it abuts on the thickened area 7, the snap-in nose 10 moves radially outwards due to the effect of the intrinsic elasticity of the material of the clamping sleeve 8 and engages in a lateral opening 11 of the head part 3. As a result, the clamping sleeve 8 is secured in the interior space 6 against any unintentional withdrawal towards the upper side. The snap-in nose 10 has, for this purpose, an upper snap-in surface 12, which extends transversely to the insertion direction of the clamping sleeve 8, on the upper side and on the underside an inclined slide-on surface 13 which abuts on the inner wall of the head part 3 when the clamping sleeve 8 is inserted and, as a result, bends the snap-in nose 10 elastically inwards.

The clamping sleeve 8 has on oppositely located sides U-shaped recesses 14 which are open towards the upper side and the edges of which form a contact surface for a cylindrical retaining bar 15 which can be inserted into the clamping sleeve 8 from above through the recess 14 so that the longitudinal axis of the retaining bar 15 extends transversely to the longitudinal axis of the clamping sleeve 8. Two corresponding openings which are open upwards are provided in the head part 3 and the retaining bar 15 can pass through them when it is place in the receiving surface of the recess 14.

A retaining ring 17 is placed on the upper edge 16 of the head part 3 and this ring abuts on the inner side of the interior space 6 with an inner surface 18 and on its outer side with an outer surface 19 extending parallel thereto; the inner surface 18 and the outer surface 19 are connected by an annular end surface 20 which rests on the upper edge 16 of the head part 3. The inner surface 18 and the inner wall of the interior space 6 in the area covered by the inner surface 18 have circumferential grooves or circumferential channels 21 and 22, respectively, which extend all the way around, engage in one another in a form-locking manner and, as a result, secure the retaining ring 17 on the head part 3 in an axial direction.

The retaining ring 17 surrounds a screw sleeve 23. An outer surface 24 of the screw sleeve 23 is designed to be slightly conical and has a smaller diameter towards the top. This outer surface 24 abuts on an inner surface 25 of the retaining ring 17 which is of a complementary shape. The screw sleeve 23 has a continuous bore 26 with an internal thread, into which a clamping screw 27 can be screwed from the upper side. This screw has an internal polyhedron 28 for the insertion of a rotary tool as well as an extension 29 which adjoins this on the upper side and makes the insertion of the rotary tool into the internal polyhedron 28 easier.

On its underside, the clamping screw 27 has in its center a spherical projection 30 which snaps elastically into a correspondingly spherical recess 31 of a pressure element 32 so that the clamping screw 27 and the pressure element 32 are permanently connected to one another but freely rotatable relative to one another.

The pressure element 32 has the shape of an elastically deformable plate or a disc which extends over the entire interior space 6 and comes to rest on the upper edge 34 of the clamping sleeve 8 with its outer edge 33 when the clamping screw 27 is screwed into the screw sleeve 23. As a result of this abutment, the elastic pressure element 32 presses the clamping sleeve 8 against the thickened area 7 of the threaded shaft 2 which, as a result, is pressed against the constriction 5 and clamped in relation to the head part 3. This pressing force restricts the free pivotability of the thickened area 7 in the head part 3; this may be between a slight restriction and a complete blocking, depending on the pressing force.

The elastic pressure element 32 is shaped and arranged such that it maintains a distance from the retaining bar 15 inserted into the recess 14 of the clamping sleeve 8 when it first abuts on the upper edge 34 of the clamping sleeve 8 and so, first of all, only the clamping sleeve 8 is moved downwards when the clamping screw 27 is screwed in and leads to clamping of the thickened area 7, as illustrated in FIG. 3.

When the clamping screw 27 is screwed in further, however, the elastic pressure element 32 is deformed in such a manner that the central area is displaced downwards in relation to the outer edge 33 and abuts on the upper side of the retaining bar 15, as illustrated in FIG. 4. As a result, the retaining bar 15 is pressed into the recess 14 of the clamping sleeve 8 and, therefore, clamped in relation to the clamping sleeve 8. At the same time, the clamping sleeve 8 is, as a result, pressed, in addition, forcefully against the thickened area 7 and so the clamping action of the clamping sleeve 8 is also increased in relation to the pressing forces caused solely by the pressure element 32. In this position, head part, threaded shaft and retaining bar are clamped together to form a rigid unit.

The user can generate, first of all, a weak and then an increasingly secure clamping of the thickened area 7 in the head part 3 simply by turning the clamping screw 27, first of all without securing the retaining bar 15 in position and, when the clamping screw 27 is turned in further, also with clamping of the retaining bar 15 until a clamping position is reached at the maximum screw-in depth of the clamping screw 27 which tensions the entire assembly against any movement.

The arrangement described is selected such that the retaining ring 17, the screw sleeve 23 as well as the clamping screw 27 with the pressure element 32 can be inserted into the head part 3 from above as a preassembled component unit; in this respect, the clamping screw 27 must, of course, be screwed out of the screw sleeve 23 to such an extent that the clamping sleeve 8 and the retaining bar 15 are not yet clamped in place when the retaining ring 17 is pushed completely into the interior space 6 until its end surface 20 is supported on the upper edge of the head part 3.

In the embodiment illustrated, the clamping screw 27 is held in the retaining ring 17, which absorbs the forces directed radially outwards and, therefore, secures the head part 3 against any undesired spreading apart, via a conical clamping.

It would, of course, also be possible to use a modified assembly, for example, a clamping screw 27 which is screwed directly into an internal thread of the interior space 6 and bears an elastically deformable pressure element 32 in the manner described.

The elastically deformable pressure element 32 need also not necessarily be connected to the clamping screw 27; it could also be a loosely inserted spring washer which is supported on the upper edge 34 of the clamping sleeve 8 and against the center of which the clamping screw 27 presses from above when the clamping screw 27 is screwed in.

What is claimed is:

1. Orthopedic retaining system comprising:
   at least one bone screw having a head part and a threaded shaft pivotally mounted on the head part,
   a clamping element mounted in the head part, the clamping element adapted to be pressed against threaded shaft from an upper side of the head part and thereby securing the threaded shaft relative to the head part,
   a retaining bar arranged in a receptacle of the head part and extending essentially transversely to the threaded shaft, and
   a clamping device on the upper side of the head part for pressing the clamping element and the retaining bar into the head part in such a manner that the threaded shaft and the retaining bar are secured in position relative to the head part,
   the clamping device comprising an elastically deformable pressure element, the pressure element which, upon actuation of the clamping device in a direction of displacement towards the underside of the head part, is displaced into a clamping position,
   wherein:
      the pressure element is elastically deformable in the direction of displacement,
   and
      upon actuation of the clamping device and the resulting displacement of the pressure element into the clamping position, the pressure element abuts first on the clamping element and thereby secures the pivotable threaded shaft in position on the head part while the retaining bar remains freely displaceable, and only upon further actuation of the clamping device in the direction of displacement is the pressure element elastically deformed, thereby abutting on the retaining bar and securing the retaining bar in position.

2. Orthopedic retaining system as defined in claim 1, wherein the retaining bar rests on the clamping element.

3. Orthopedic retaining system as defined in claim 1, wherein:
   the clamping device comprises an actuating element displaceable relative to the head part, and
   the actuating element engages on the pressure element and moves the pressure element in the displacement direction towards the clamping position.

4. Orthopedic retaining system as defined in claim 3, wherein the actuating element is a clamping screw adapted to be screwed into the head part from the upper side.

5. Orthopedic retaining system as defined in claim 1, wherein the pressure element is an elastic bracket bridging an interior space of the head part, ends of said bracket being held on the clamping element.

6. Orthopedic retaining system as defined in claim 1, wherein the pressure element is an elastically deformable disc, an edge of said disc being held on the clamping element.

7. Orthopedic retaining system as defined in claim 3, wherein the actuating element engages a central area of the pressure element.

8. Orthopedic retaining system as defined in claim 5, wherein the actuating element engages a central area of the pressure element.

9. Orthopedic retaining system as defined in claim 6, wherein the actuating element engages a central area of the pressure element.

10. Orthopedic retaining system as defined in claim 7, wherein the pressure element and the actuating element are designed in one piece.

11. Orthopedic retaining system as defined in claim 7, wherein the pressure element and the actuating element are designed in one piece.

12. Orthopedic retaining system as defined in claim 1, wherein the pressure element and the actuating element are releasably connected to one another.

13. Orthopedic retaining system as defined in claim 12, wherein the releasable connection is an elastic snap-in connection.

14. Orthopedic retaining system as defined in claim 4, wherein the pressure element and the actuating element are rotatable relative to one another.

15. Orthopedic retaining system as defined in claim 1, wherein the clamping element is a sleeve supported on the threaded shaft with a lower edge, the pressure element resting on an upper edge of the sleeve.

16. Orthopedic retaining system as defined in claim 3, wherein the clamping element is a sleeve supported on the threaded shaft with a lower edge, the pressure element resting on an upper edge of the sleeve.

17. Orthopedic retaining system as defined in claim 7, wherein the clamping element is a sleeve supported on the threaded shaft with a lower edge, the pressure element resting on an upper edge of the sleeve.

* * * * *